(12) United States Patent
Fayram

(10) Patent No.: US 7,725,186 B1
(45) Date of Patent: May 25, 2010

(54) COMPLIMENTARY ACTIVITY SENSOR NETWORK FOR DISEASE MONITORING AND THERAPY MODULATION IN AN IMPLANTABLE DEVICE

(75) Inventor: Timothy A. Fayram, Gilroy, CA (US)

(73) Assignee: Pace Setter, Inc., Sunnyvale, CA (US)

(*) Notice: Subject to any disclaimer, the term of this patent is extended or adjusted under 35 U.S.C. 154(b) by 526 days.

(21) Appl. No.: 11/565,348

(22) Filed: Nov. 30, 2006

Related U.S. Application Data

(62) Division of application No. 11/003,203, filed on Dec. 3, 2004, now Pat. No. 7,155,281.

(51) Int. Cl.
*A61N 1/37* (2006.01)
*A61B 5/0205* (2006.01)

(52) U.S. Cl. .................... 607/18; 607/22; 600/547; 600/323

(58) Field of Classification Search ......... 600/506, 600/513, 547, 587, 595, 301, 323, 483; 607/17, 607/18, 22
See application file for complete search history.

(56) References Cited

U.S. PATENT DOCUMENTS

| | | | |
|---|---|---|---|
| 4,140,132 A | 2/1979 | Dahl | |
| 4,428,378 A | 1/1984 | Anderson et al. | |
| 4,485,813 A | 12/1984 | Anderson et al. | |
| 4,860,751 A * | 8/1989 | Callaghan | 607/16 |
| 4,905,697 A | 3/1990 | Heggs et al. | |
| 5,065,759 A | 11/1991 | Begemann et al. | |
| 5,097,831 A | 3/1992 | Lekholm | |
| 5,101,824 A | 4/1992 | Lekholm | |
| 5,342,404 A | 8/1994 | Alt et al. | |
| 5,350,412 A | 9/1994 | Hoegnelid et al. | |
| 5,376,106 A | 12/1994 | Stahmann | |
| 5,383,473 A | 1/1995 | Moberg | |
| 5,387,229 A | 2/1995 | Poore | |
| 5,413,592 A | 5/1995 | Schroeppel | |
| 5,423,869 A | 6/1995 | Poore et al. | |
| 5,425,750 A * | 6/1995 | Moberg | 607/19 |
| 5,441,524 A | 8/1995 | Rueter et al. | |
| 5,527,345 A | 6/1996 | Infinger | |
| 5,573,003 A | 11/1996 | Mann et al. | |
| 5,626,622 A | 5/1997 | Cooper | |
| 5,755,740 A | 5/1998 | Nappholz | |
| 5,766,228 A | 6/1998 | Bonnet | |
| 5,792,199 A | 8/1998 | Fayram et al. | |
| 5,807,283 A * | 9/1998 | Ng | 600/595 |
| 5,833,713 A | 11/1998 | Moberg | |
| 6,002,963 A | 12/1999 | Mouchawar et al. | |
| 6,023,641 A | 2/2000 | Thompson | |
| 6,055,454 A | 4/2000 | Heemels | |

(Continued)

*Primary Examiner*—Carl H Layno
*Assistant Examiner*—Natasha N Patel
(74) *Attorney, Agent, or Firm*—Steven M. Mitchell

(57) ABSTRACT

Energy efficient methods and systems for using multi-dimensional activity sensors with implantable cardiac devices are provided. In certain embodiments the output of a passive activity sensor (used for rate responsive pacing) is used to trigger temporary use of a relatively high power multi-dimensional activity sensor. In other embodiments, the output of a relatively low power oxygen saturation sensor is used to trigger temporary use of a relatively high power multi-dimensional activity sensor. This description is not intended to be a complete description of, or limit the scope of, the invention.

19 Claims, 5 Drawing Sheets

U.S. PATENT DOCUMENTS

| | | | |
|---|---|---|---|
| 6,163,723 A * | 12/2000 | Roberts et al. .................. 607/18 |
| 6,167,303 A | 12/2000 | Thompson |
| 6,185,454 B1 | 2/2001 | Thompson |
| 6,185,460 B1 | 2/2001 | Thompson |
| 6,223,080 B1 | 4/2001 | Thompson |
| 6,275,727 B1 | 8/2001 | Hopper et al. |
| 6,275,733 B1 | 8/2001 | Park et al. |
| 6,277,078 B1 | 8/2001 | Porat et al. |
| 6,363,280 B1 | 3/2002 | Mouchawar et al. |
| 6,459,929 B1 | 10/2002 | Hopper et al. |
| 6,466,821 B1 | 10/2002 | Pianca et al. |
| 6,472,991 B1 | 10/2002 | Schulman et al. |
| 6,480,733 B1 | 11/2002 | Turcott |
| 6,491,639 B1 | 12/2002 | Turcott |
| 6,658,292 B2 | 12/2003 | Kroll et al. |
| 6,662,047 B2 | 12/2003 | Sorensen et al. |
| 6,741,885 B1 | 5/2004 | Park et al. |
| 2004/0260346 A1 | 12/2004 | Overall et al. |

* cited by examiner

COMPLIMENTARY ACTIVITY SENSOR NETWORK FOR DISEASE MONITORING AND THERAPY MODULATION IN AN IMPLANTABLE DEVICE

PRIORITY CLAIM

This application is a Divisional of and claims priority to U.S. patent application Ser. Nos. 11/003,203, filed Dec. 3, 2004, entitled "Complimentary Activity Sensor Network for Disease Monitoring and Therapy Modulation in an Implantable Device", which is incorporated herein by reference.

FIELD OF THE INVENTION

Embodiments of the present invention relate to implantable medical devices that include sensors for obtaining non-physiologic data (e.g., activity data).

BACKGROUND

A pacemaker is an implantable medical device which delivers electrical stimulation pulses to cardiac tissue to relieve symptoms associated with bradycardia—a condition in which a patient cannot maintain a physiologically acceptable heart rate. Early pacemakers delivered stimulation pulses at regular intervals in order to maintain a predetermined heart rate, which was typically set at a rate deemed to be appropriate for the patient at rest. The predetermined rate was usually set at the time the pacemaker was implanted, and in more advanced devices, could be set remotely after implantation.

Early advances in pacemaker technology included the ability to sense a patient's intrinsic cardiac activity (i.e., the intercardiac electrogram, or "IEGM"). This led to the development of "demand pacemakers," so named because these devices deliver stimulation pulses only as needed by the heart. Demand pacemakers are capable of detecting a spontaneous, hemodynamically effective, cardiac contraction which occurs within a predetermined time period (commonly referred to as the "escape interval") following a preceding contraction. When a naturally occurring contraction is detected within the escape interval, a demand pacemaker does not deliver a pacing pulse. The ability of demand pacemakers to avoid delivery of unnecessary stimulation pulses is desirable, because it extends battery life.

Pacemakers such as those described above proved to be extremely beneficial in that they successfully reduced or eliminated seriously debilitating and potentially lethal effects of bradycardia in many patients. However, the early devices were not adjustable "in the field"—that is, the heart rates maintained by these devices were not adjustable in accordance with changing levels of physical exertion. Thus, during periods of elevated physical activity, some patients were subject to adverse physiological consequences, including lightheadedness and episodes of fainting, because their heart rates were forced by the pacemaker to remain constant at an inappropriately low rate. Also, some patients were subject to discomfort resulting from heart rates that were maintained higher than would normally be appropriate during periods of rest.

A major advance in pacemaker technology was the development of "rate-responsive pacemakers." These devices are capable of adjusting the patient's heart rate in accordance with metabolic demands, even as those demands vary as a result of changing levels of physical exertion. Rate-responsive pacemakers typically maintain a predetermined minimum heart rate when the patient is engaged in physical activity at or below a threshold level, and gradually increase the maintained heart rate in accordance with increased levels of physical activity until a maximum rate is reached. In many rate-responsive pacemakers, the minimum heart rate, maximum heart rate, and the slope or curve between the minimum heart rate and the maximum heart rate are programmable, so that they may be configured to meet the needs of a particular patient.

In order to provide rate-responsive pacing therapy, a pacemaker must be capable of correlating an indicator of physical activity to an appropriate heart rate. The generally accepted technique for providing rate-responsive pacing is to employ sensors that transduce mechanical forces associated with physical activity. A widely used sensor of this type incorporates a piezoelectric crystal which generates a measurable electrical potential when a mechanical stress resulting from physical activity is applied to the sensor. U.S. Pat. No. 4,140,132 to Dahl and U.S. Pat. No. 4,428,378 to Anderson et al., which are incorporated herein by reference, describe examples of rate-responsive pacemakers that maintain a patient's heart rate in accordance with physical activity as measured by a piezoelectric sensor incorporating a piezoelectric crystal. Besides piezoelectric crystals, other piezoelectric activity sensors employed in pacemakers use a cantilever beam having a film of a piezoelectric polymer adhered to a surface of the beam. Examples of such cantilever type passive sensor are described in U.S. Pat. No. 5,833,713 to Moberg and U.S. Pat. No. 5,383,473 to Moberg, which are incorporated herein by reference.

Piezoelectric activity sensors are passive devices, meaning they do not require an external excitation current or voltage to operate. Rather, they convert mechanical motion into a detectable electrical signal, such as a back electro magnetic field (BEMF) current or voltage. Accordingly, since minimizing current drain and power consumption is critical with battery powered implantable devices, piezoelectric activity sensors are the primary type of activity sensor used in rate-responsive pacemakers. Nevertheless, despite their widespread use, piezoelectric activity sensors have certain limitations. For example, a typical passive piezoelectric activity sensor is only able to provide one dimension of information, i.e., acceleration. While this may be enough information to provide acceptable rate responsive pacing, it would be beneficial if the dynamic and spatial range of information obtained from activity sensors could be increased.

More specifically, it would be beneficial if more complex and informative trends about a patient's physical activity, or lack thereof, can be obtained. Such information may be indicative of how often the patient is active over a specified period of time, or even how often the patient is lying down, sitting up, walking and/or running. This type of information may be very beneficial to a physician that is monitoring the progression of a disease, such as congestive heart failure (CHF). CHF is a disease in which abnormal function of the heart leads to inadequate blood flow to fulfill the needs of the body's tissues, resulting in fatigue, weakness, and inability to carry out daily tasks.

More complex multi-dimension activity sensors have been proposed. For example, U.S. Pat. No. 6,658,292 to Kroll et al. describes a three dimensional accelerometer-based position sensor that can sense a patient's movement, position and activity status, such as whether the patient is ascending/descending stairs or is sitting up from a lying position, based on the vertical velocity and minute ventilation data. For another example, U.S. Pat. No. 6,466,821 to Pianca et al. describes an AC/DC multi-axis accelerometer that can also be used to determine patient activity and body position. An example of a commercially available dual-axis accelerometer is the model ADXL210 available from Analog Devices of Norwood, Mass. While there would be informational advantages to including such multi-dimensional activity sensors in a pacemaker, such sensors typically require a current in the range of 0.1 mA or greater (in contrast, the parasitic current associated with a passive piezoelectric activity sensor is in the range of about 5 to 15 µA, i.e., 0.005 to 0.015 mA). Since minimizing current drain and power consumption is critical with battery powered implantable devices, it has not yet been practical to include such relatively high powered multi-dimensional activity sensors within pacemakers.

Chronic diseases such as CHF require close medical management to reduce morbidity and mortality. Because the disease status evolves with time, frequent physician follow-up examinations are often necessary. At follow-up, the physician may make adjustments to the drug regimen in order to optimize therapy. This conventional approach of periodic follow-up is unsatisfactory for some diseases, such as CHF, in which acute, life-threatening exacerbations can develop between physician follow-up examinations. It is well know among clinicians that if a developing exacerbation is recognized early, it can be more easily and inexpensively terminated, typically with a modest increase in oral diuretic. However, if it develops beyond the initial phase, an acute heart failure exacerbation becomes difficult to control and terminate. Hospitalization in an intensive care unit is often required. It is during an acute exacerbation of heart failure that many patients succumb to the disease.

It is often difficult for patients to subjectively recognize a developing exacerbation, despite the presence of numerous physical signs that would allow a physician to readily detect it. Furthermore, since exacerbations typically develop over hours to days, even frequently scheduled routine follow-up with a physician cannot effectively detect most developing exacerbations. It is therefore desirable to have a system that allows the routine, frequent monitoring of patients so that an exacerbation can be recognized early in its course. With the patient and/or physician thus notified by the monitoring system of the need for medical intervention, a developing exacerbation can easily and inexpensively be terminated early in its course.

Accordingly, it would be advantageous to provide implantable cardiac devices that can obtain complex and informative trends about a patient's physical activity, or lack thereof, while keeping the current drain and power consumption within an acceptable range. More generally, it is desirable to provide implantable cardiac devices that can obtain disease progression information in an energy efficient manner.

SUMMARY OF THE INVENTION

Embodiments of the present invention are directed to implantable stimulation devices, and methods for use therewith, that can be used to obtain complex and informative trends about a patient's physical activity, or lack thereof, in an energy efficient manner. More specifically, such information may be indicative of how often the patient is active over a specified period of time, or even how often the patient is lying down, sitting up, walking and/or running. This type of information may be very beneficial to a physician that is monitoring the progression of a disease, such as congestive heart failure (CHF). Such information may also be useful for triggering an alert that is indicative of a developing exacerbation.

In accordance with an embodiment of the present invention, a passive activity sensor is used to continually produce a signal indicative of one dimension of activity that is used for rate responsive pacing. The passive activity sensor, e.g., a piezoelectric device, does not require an external excitation current for it to produce its signal, and is thus very energy efficient. However, limited analysis can be based on the one dimension of activity (e.g., acceleration) that is monitored using the passive activity. Accordingly, an active activity sensor is used to intermittently monitor at least two dimensions of activity that are useful for monitoring disease progression by producing one or more signal indicative of the at least two dimension of activity. Such an active activity sensor requires an external excitation current, e.g., of at least 0.7 mA, to produce its one or more signal indicative of the at least two dimensions of activity. By only using the active activity sensor intermittently, valuable more informative information can be obtained in an energy efficient manner.

In accordance with an embodiment of the present invention, the intermittent use of the active activity sensor is triggered in response the passive activity sensor sensing at least a predetermined amount of activity. Alternatively or additionally, the active activity sensor can be used in accordance with a specified duty cycle.

In an embodiment, data and timing information, indicative of the at least two dimensions of activity monitored using the active activity sensor, are stored. This stored data and timing information can then be analyzed to quantify a patient's activity level over a specified period of time. Then, in accordance with an embodiment of the present invention, an alert can be triggered in response to a determination that the patient's activity level over the specified period of time drops below a specified level.

In accordance with another embodiment of the present invention, a first sensor is used to monitor a patient's oxygen saturation level, wherein the first sensor requires a first external excitation current to monitor oxygen saturation level. Use of a multi-dimensional activity sensor is triggered when the monitored oxygen saturation level drops below a specified level. Such a multi-dimensional activity sensor, which monitors at least two dimensions of activity that are useful for monitoring disease progression, requires a second excitation current to produce one or more signal indicative of the at least two dimensions of activity, where the second excitation current is greater than the first external excitation current. In a similar manner as described above, data and timing information, indicative of the at least two dimensions of activity monitored using the active activity sensor, can be stored, analyzed, and used to trigger an alert.

This description is not intended to be a complete description of, or limit the scope of, the invention. Other embodiment, features and advantages of the invention will appear from the following description in which the preferred embodiments have been set forth in detail, in conjunction with the accompanying drawings and claims.

DETAILED DESCRIPTION

Exemplary Pacing Device

Figure 1:
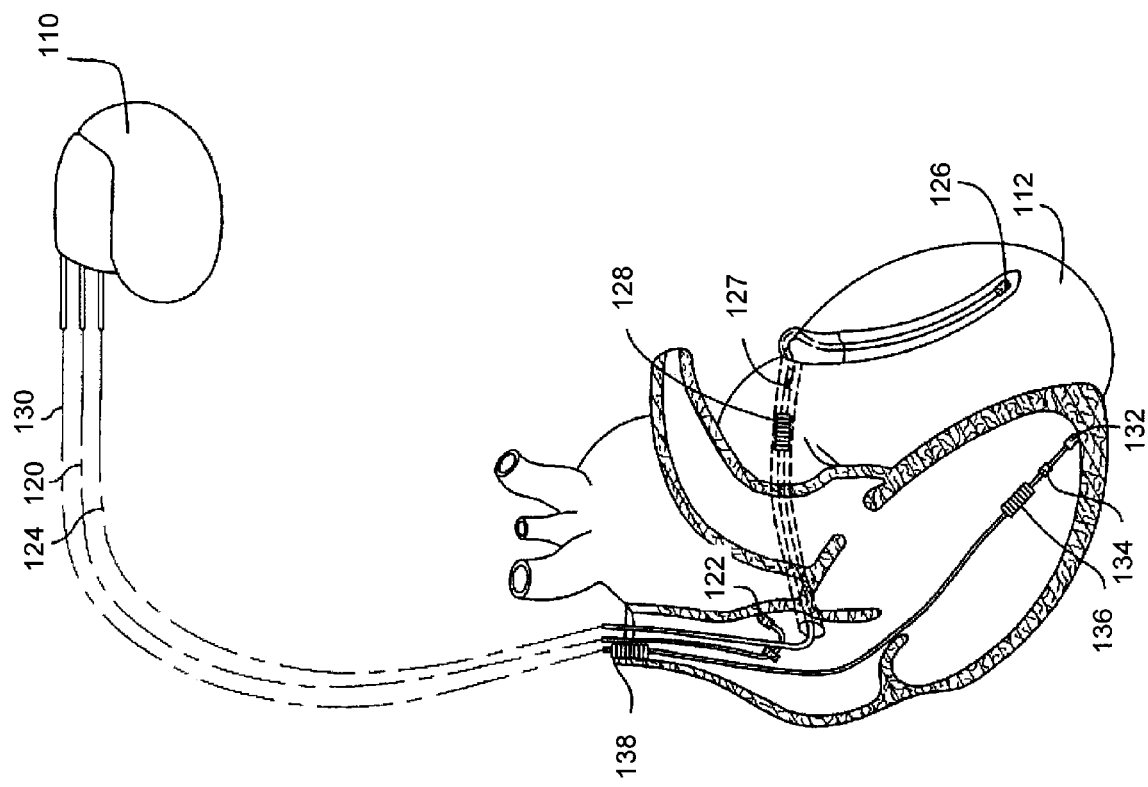
FIG. 1 illustrates an exemplary implantable stimulation device in electrical communication with a patient's heart by way of three leads, which are suitable for delivering multi-chamber stimulation and shock therapy.

Before describing specific embodiments of the present invention, it is useful to first describe an exemplary environment in which the invention may be implemented. Referring to FIG. 1, an exemplary implantable cardiac device 110 (also referred to as a pacing device, a pacing apparatus, a stimulation device, or simply a device) is in electrical communication with a patient's heart 112 by way of three leads, 120, 124 and 130, suitable for delivering multi-chamber stimulation. While not necessary to perform embodiments of the present invention, the exemplary device 110 is also capable of delivering shock therapy.

To sense atrial cardiac signals and to provide right atrial chamber stimulation therapy, the stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. Embodiments of the present invention may of course be practiced with a coronary sinus lead that does not include left atrial sensing, pacing or shocking electrodes.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. It will be understood by those skilled in the art that other lead and electrode configurations such as epicardial leads and electrodes may be used.

Figure 2:
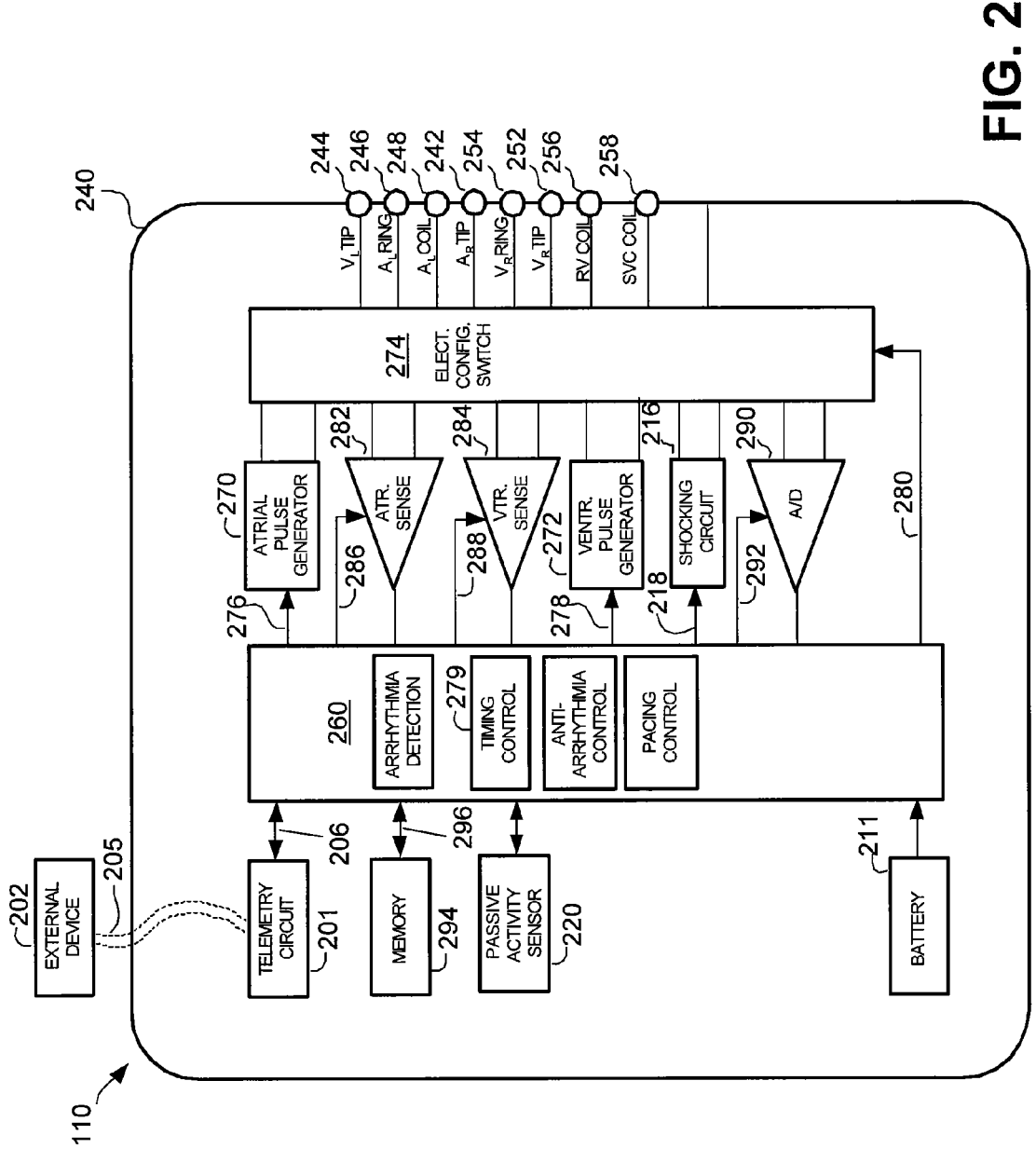
FIG. 2 is a simplified block diagram showing additional details of the exemplary multi-chamber implantable stimulation device of FIG. 1.

As illustrated in FIG. 2, a simplified block diagram is shown of the multi-chamber implantable pacing device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the pacing device 110, shown schematically in FIG. 2, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 122.

To achieve left atrial and ventricle sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 148, which are adapted for connection to the left ventricular ring electrode 126, the left atrial tip electrode 127, and the left atrial coil electrode 128, respectively.

To support right ventricle sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 132, right ventricular ring electrode 134, the RV coil electrode 136, and the SVC coil electrode 138, respectively.

At the core of the pacing device 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with arrhythmia detection, selecting an appropriate anti-arrhythmia therapy, performing a mode switch from an atrial tracking ventricular pacing mode to a non-atrial tracking ventricular pacing mode, as well as maintaining a high percentage of pacing during mode switch.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators, or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

A passive activity sensor 220 is used to obtain information relating to the physical activity of the patient. As mentioned above, a passive activity sensor devices 220 can convert mechanical motion into a detectable electrical signal (e.g., a BEMF signal) without requiring an external excitation current or voltage. However, it is noted that some parasitic current will still be necessary to measure the electrical signal produced by the activity sensor 220. Such parasitic current is typically very low, e.g., on the order of 5 to 15 µA.

As mentioned above, a widely used passive activity sensor incorporates a piezoelectric crystal which generates a measurable electrical potential when a mechanical stress resulting from physical activity is applied to the sensor. Examples of these are described in U.S. Pat. No. 4,140,132 to Dahl and U.S. Pat. No. 4,428,378 Anderson et al., which were incorporated by reference above. Another type of passive activity sensor 220 includes use a cantilever beam having a film of a piezoelectric polymer adhered to a surface of the beam, rather than a piezoelectric crystal. Example of this are described in U.S. Pat. Nos. 5,833,713 and 5,383,473 to Moberg, which were incorporated by reference above. A further type of passive activity sensor 220 includes a magnet assembly and a conductive coil that moves relative to the magnet assembly in response to motion. An example of this is described in U.S. Pat. No. 5,792,199 to Fayram et al., which is incorporated herein by reference. These are just a few examples of the types of passive activity sensor 220 that could be included within the device 110. Using one dimensional activity information (i.e., acceleration) obtained by the passive activity sensor 220, the microcontroller 260 can deliver rate-responsive pacing.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation. Such sensing circuits, 282 and 284, can be used to determine cardiac performance values used in the present invention. Alternatively, an automatic sensitivity control circuit may be used to effectively deal with signals of varying amplitude.

The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity, in the appropriate chambers of the heart. The sensing circuits, 282 and 284, in turn, receive control signals over signal lines, 286 and 288, from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 286.

For arrhythmia detection, the device 110 utilizes the atrial and ventricular sensing circuits, 282 and 284, to sense cardiac signals to determine whether a rhythm is physiologic or pathologic. The timing intervals between sensed events (e.g., P-waves, R-waves, and depolarization signals associated with fibrillation) are then classified by the microcontroller 260 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 202. The data acquisition system 290 is coupled to the right atrial lead 120, the coronary sinus lead 124, and the right ventricular lead 130 through the switch 274 to sample cardiac signals across any pair of desired electrodes.

Advantageously, the data acquisition system 290 can be coupled to the microcontroller 260, or other detection circuitry, for detecting an evoked response from the heart 212 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 260 is further coupled to a memory 294 by a suitable data/address bus 296, wherein the programmable operating parameters used by the microcontroller 260 are stored and modified, as required, in order to customize the operation of the pacing device 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 212 within each respective tier of therapy Advantageously, the operating parameters of the implantable device 110 may be non-invasively programmed into the memory 294 through a telemetry circuit 201 in telemetric communication with the external device 202, such as a programmer, transtelephonic transceiver, or a diagnostic system analyzer. The telemetry circuit 201 can be activated by the microcontroller 260 by a control signal 206. The telemetry circuit 201 advantageously allows intracardiac electrograms and status information relating to the operation of the device 110 (as contained in the microcontroller 260 or memory 294) to be sent to an external device 202 through an established communication link 204.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

In the case where the pacing device 110 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses of low (up to 0.5 Joules), moderate (0.5-10 Joules), or high energy (11 to 40 Joules), as controlled by the microcontroller 260. Such shocking pulses are applied to the patient's heart 212 through at least two shocking electrodes, and as shown in this embodiment, selected from the left atrial coil electrode 228, the RV coil electrode 236, and/or the SVC coil electrode 238. As noted above, the housing 240 may act as an active electrode in combination with the RV electrode 236, or as part of a split electrical vector using the SVC coil electrode 238 or the left atrial coil electrode 228 (i.e., using the RV electrode as a common electrode).

The pacing device 110 additionally includes a battery 211 which provides operating power to all of the circuits shown in FIG. 2. If the pacing device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected.

The above described stimulation device 110 was described as an exemplary pacing device. One or ordinary skill in the art would understand that embodiments of the present invention can be used with alternative types of implantable cardiac devices. Accordingly, embodiments of the present invention should not be limited to use only with the above described device.

Energy Efficient Use of Active Activity Sensors for Monitoring Disease Progression As explained above, it would be beneficial if implantable cardiac devices (e.g., 110) can obtain complex and informative trends about a patient's physical activity, or lack thereof, while keeping the current drain and power consumption within an acceptable range. More generally, it is desirable to provide implantable cardiac devices that can obtain disease progression information in an energy efficient manner.

An example of a disease for which physicians want to monitor progression is congestive heart failure (CHF), which a debilitating disease in which abnormal function of the heart leads to inadequate blood flow to fulfill the needs of the body's tissues. Fatigue, weakness, and inability to carry out daily tasks may result. Not all CHF patients suffer debilitating symptoms immediately. Some may live actively for years. Yet, with few exceptions, the disease is relentlessly progressive.

CHF has been classified by the New York Heart Association (NYHA) into four stages or classes of progressively worsening symptoms and exercise capacity, i.e., from Class I to Class IV. Class I corresponds to no limitation wherein ordinary physical activity does not cause undue fatigue, shortness of breath, or palpitation. Class II corresponds to slight limitation of physical activity wherein such patients are comfortable at rest, but where ordinary physical activity results in fatigue, shortness of breath, palpitations, or angina. Class III corresponds to a marked limitation of physical activity wherein, although patients are comfortable at rest, less than ordinary activity will lead to symptoms. Lastly, Class IV corresponds to inability to carry on any physical activity without discomfort, wherein symptoms of CHF are present even at rest and where with any physical activity, increased discomfort is experienced.

Current standard treatment for CHF is typically centered around medical treatment using ACE inhibitors, diuretics, and digitalis. It has also been demonstrated that aerobic exercise may improve exercise tolerance, improve quality of life, and decrease symptoms. Although advances in pharmacological therapy have significantly improved the survival rate and quality of life of CHF patients, patients in NYHA Classes III or IV, who are still refractory to drug therapy, have a poor prognosis and limited exercise tolerance. Cardiac pacing has been proposed as a new primary treatment for patients with drug-refractory CHF.

By tracking the progression or regression of CHF more closely, treatments could be administered more effectively. Commonly, patients adapt their lifestyle and activities to their physical condition. The activity level of the patients with NYHA Class III or IV would be much lower than that of the patients with NYHA Class I or II. The change in lifestyle or activity level, due to the patient's heart condition, will be reflected by physiological parameters, such as activity. It will be understood from the description herein that embodiments of the present invention can be used to track CHF (as well as other disease) progression or regression to enhance the administration of therapies and to enable the monitoring of the effectiveness of such therapies.

Patients with CHF are often unable to maintain adequate blood flow throughout their circulatory system. This causes excess fluid pressure within the blood vessels, which can lead to edema. More specifically, left-sided CHF can cause pulmonary edema, as fluid shifts into the lungs. Patients with pulmonary edema may develop rapid, shallow respirations, shortness of breath, and a cough. Right-sided CHF can cause peripheral edema (also known as extremity edema), which results in a swelling in the tissue under the skin of the lower legs and feet.

A patient's leg muscles normally contract and compress blood vessels to promote blood flow with walking or running. When these muscles are not used, blood can collect in the veins, making it difficult for fluid to move from tissues back into the vessels. Accordingly, CHF patients' that are at risk of edema are typically instructed to exercise on a regular basis, in an attempt to mitigate edema. However, even though physicians will ask their patients' whether they have kept up with their recommended exercise schedule, patients often overestimate their level of exercise (due to the subjective nature of such inquiries), or blatantly do not tell the truth to their physician. It would be beneficial if quantifiable information relating to patient activity, or lack thereof, can be collected for review by a physician.

A symptom of both pulmonary edema and peripheral edema is that a patient become lethargic and their activity level significantly decreases. Treatments for edema include, e.g., use of diuretics and other medications to rid the patient of excess fluids, restriction of salt intake and treatment of the underlying condition that caused the edema. When edema occurs it is important to treat the edema, or the underlying condition causing the edema, so that it does not lead to even more severe problems. Accordingly, it would be beneficial for patients and/or a physicians to be alerted of edema so that the patient and/or physician can respond appropriately. For example, a patient may be instructed to visit his physician when such an alert occurs, or to use a diuretic, or to increase a dosage of diuretic.

Figure 3:
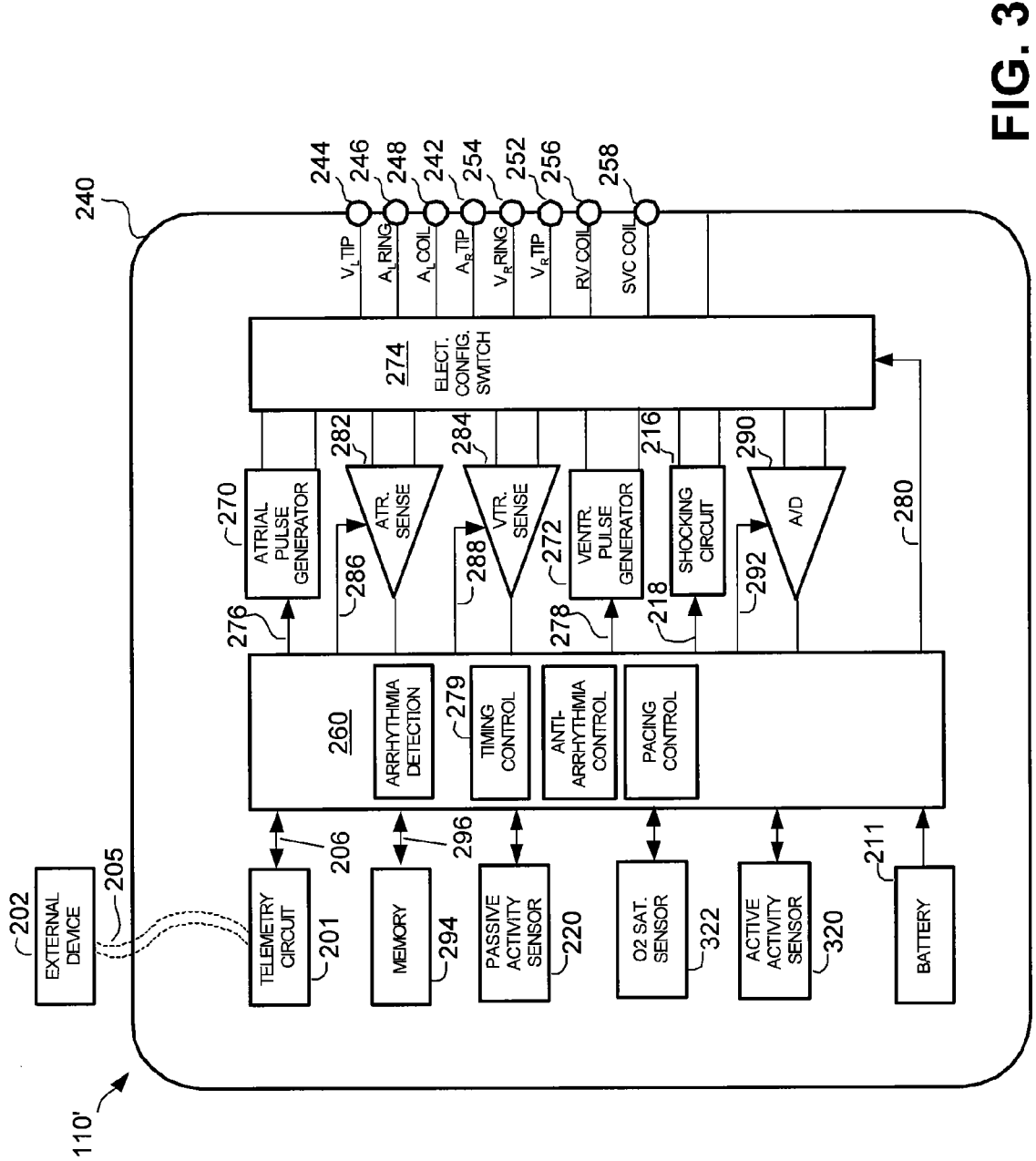
FIG. 3 illustrates the device of FIG. 2 modified in accordance with an embodiment of the present invention.

Referring now to FIG. 3, in accordance with embodiments of the present invention, the implantable pacing device (labeled 110' in FIG. 3) also includes an active activity sensor 320 which is useful for measuring multi-dimensional activity information. For example, the active activity sensor 320 may be used to measure two or more of the following: acceleration, direction, posture and tilt. Sensor 320 is referred to as being "active" since it requires an external excitation current or voltage to produce one or more signal that is indicative of activity.

In contrast, a passive activity sensor (e.g., 220) does not require an external excitation current or voltage to operate, as was mentioned above. Rather, a passive sensor converts mechanical motion into a detectable electrical signal, such as a back electro magnetic field (BEMF) current or voltage, without requiring any external excitation. Thus, from an energy perspective, a passive activity sensor provides an output that is indicative of activity without energy consumption. It is noted that a small amount of parasitic energy is necessary to measure the output of a passive activity sensor. However, such parasitic energy required to measure the output of a passive activity sensor is typically one or more orders of magnitude less than the amount of energy required to power an active activity sensor 320. For example, 5 to 15 µA of background current provided by a typical battery of an implantable cardiac device is sufficient to operate all of the background functions of the device, not including low voltage pacing therapies, anti tachy pacing therapies, and high voltage defibrillation therapies. A small percent of that background current will be consumed in the processing of the signal from the output of a passive activity sensor 220. In contrast, it is likely that an active activity sensor 320 requires a minimum excitation current of 0.7 mA, which is about three orders of magnitude greater than that typically required to measure the output of the passive activity sensor 220.

Examples of active activity sensors include, but are not limited to: the three dimensional accelerometer-based position sensor disclosed in U.S. Pat. No. 6,658,292 to Kroll et al.; the AC/DC multi-axis accelerometer disclosed in U.S. Pat. No. 6,466,821 to Pianca et al.; and the commercially available precision dual-axis accelerometer model ADXL203 available from Analog Devices of Norwood, Mass.

Figure 4:
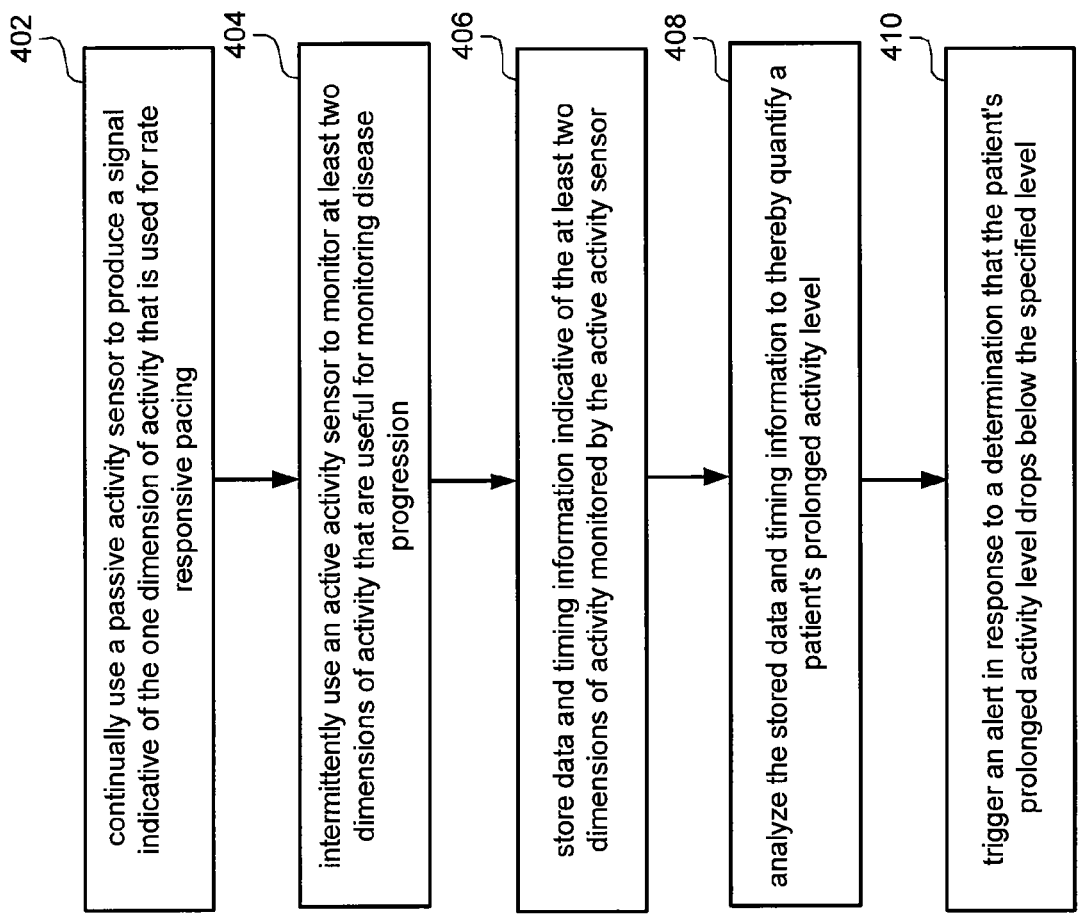
FIGS. 4 and 5 are high level flow diagrams that are useful for describing specific embodiments of the present invention.

FIG. 4 is a high level flow diagram that is useful for describing specific embodiments of the present invention that enable an implantable pacemaker to obtain complex and informative trends about a patient's physical activity, or lack thereof, while keeping the current drain and power consumption within an acceptable range.

As shown at step 402 in FIG. 4, a passive activity sensor (e.g., 220) is used (e.g., continually) to produce a signal indicative of one dimension of activity (e.g., acceleration) that is used for rate responsive pacing. As described above, such a passive activity sensor does not require an external excitation current to produce its signal. Accordingly, continual production of the signal indicative of one dimension of activity does not consume any power. It is noted that a parasitic current is required to measure the signal produced by the passive activity sensor. However, such a parasitic current is relatively low, and is approximately 0.1 µA, and less than 1 µA in the highest duty cycle applications.

As shown at step 404, an active activity sensor (e.g., 320) is used to monitor at least two dimensions of activity that are useful for monitoring disease progression (e.g., at least two of acceleration, direction, posture and tilt). An active activity sensor, as explained above, requires an external excitation current to produce one or more signal indicative of the at least two dimensions of activity. Such an excitation current is likely to be at least 0.7 mA, and depending upon how many axes are excited, may be greater than 2.0 mA. Accordingly, if the active activity sensor were always powered, the active activity sensor would cause an unacceptable drain on the battery (e.g., 211) of the implantable device. However, since the active activity sensor is only intermittently used, in accordance with embodiments of the present invention, its drain on the battery can be reduced to an acceptable level.

In accordance with specific embodiments of the present invention, step 404 includes triggering temporary use of the active activity sensor (e.g., 320) when at least a predetermined amount of activity is sensed using the passive activity sensor (e.g. 220). In other words, the active activity sensor can be temporarily enabled in response to the passive activity sensor detecting sufficient activity. This can be accomplished, e.g., by comparing amplitude measurements of the signal produced by the passive activity sensor to an appropriate threshold, such that the active activity sensor is triggered when the threshold is satisfied (e.g., reached or exceeded).

In accordance with other embodiments of the present invention, the active activity sensor is temporarily enabled whenever a specified amount of time (e.g., 20 minutes) has passed since the active activity sensor was last enabled.

Once enabled (e.g., powered using an external excitation current), the active activity sensor need only be enabled long enough (e.g., 10 seconds) that the signal(s) produced by the active activity sensor contain enough information to determine the dimensions of patient activity that are of interest.

In some embodiments, the active activity sensor can be enabled a specified amount of time (e.g., the active activity sensor is enable 33.3% of the time, and not enabled the other 66.7% of the time). In some embodiments, an amount of time between successively enabling of the active activity sensor can be specified (e.g., 1 minute), and the amount of time that the active activity sensor remains enabled (e.g., 20 seconds) can be specified. For each of just described embodiments, it can be said that the duty cycle of the active activity sensor is about 33%. These are just a few examples of how the active activity sensor can be triggered. Other ways are also within the spirit and scope of the present invention. It is preferable that the active activity sensor has a duty cycle of 50% or less. The term "duty cycle" as used herein refers to the percentage of time that a device (e.g., sensor) is drawing a current to thereby produce an output that can be measured.

At step 406, data and timing information (indicative of the at least two dimensions of activity monitored using the active activity sensor) are stored. The timing information is stored along with the activity data so that lack of activity can be monitored. In other words, by also storing timing information, lengths of periods of inactivity can be quantified. Further, by also storing timing information, periods of inactivity during normal sleeping hours can be distinguished from periods of inactivity during normal waking hours. More generally, by storing multi-dimensional activity data and corresponding timing information, a device and/or physician can determine length's of time that a patient is active, length's of time that a patient is inactive, length's of time between active periods, and the like. Storing timing information is especially important where the active activity sensor is only triggered when the passive activity sensor indicates activity that meets a threshold, because the timing information will enable determinations of amounts of time between activity sufficient to meet the threshold.

In some embodiments, step 406 includes storing the data and timing information in a memory (e.g., memory 294) within the implantable device. In other embodiments the data and timing information is transmitted (e.g., using telemetry circuit 201) to an external device that stores the data and timing information. In still other embodiments, the external device can transmit the data and timing information to another location (e.g., a central location at a hospital) where the data and timing information is stored.

At step 408, the stored data and timing information is analyzed to thereby quantify a patient's prolonged activity level (i.e., activity level over a specified period of time). In some embodiments, step 408 is performing by analyzing activity data and corresponding timing information stored over a predetermined amount of time (e.g., 1 week), and determining whether a patient's level of activity over that period of time was above or below a threshold. The analysis at step 408 can also quantify whether a patient's activity level has increased, decreases, or remained generally constant over a specified period of time. Such analysis can be accomplished in numerous ways, as will be described below. It is also possible to use multiple thresholds so that a patient's activity level can be classified into more than two levels.

Assume that the dimensions of activity being monitored using the active activity sensor include acceleration, direction and posture. From this information, periods of lying down, sitting up, walking, running, ascending stairs and descending stairs can be distinguished from one another. Such activities can be associated with activity values (e.g., 0 for lying down, 1 for sitting up, 2 for walking, 3 for running, 4 for descending stairs and 5 for ascending stairs), thereby enabling a patient's level of activity to be quantified for a period of time. Continuing with this example, the values produced over a period of time (e.g., a week) can be added to produce a total activity value that can be compared to one or more thresholds to quantify the patients level of activity for that period of time. Additionally, or alternatively, values over a period of time can be analyzed to determine whether a patient's level of activity increased, decreased or remained generally constant over a period of time.

In other embodiments, a patient's level of activity can be quantified by determining the percentage of time that a patient is lying down over a period of time. For example, if it is determined that a patient is lying down more than a certain percentage of the time (e.g., 50% of the time), then the patient can be considered to have a low level of activity. In still other embodiments, a patient's level of activity can be quantified by determining a number of periods of inactivity that exceed a length of time threshold. In further embodiments, a patients level of activity can be quantified by determining a percentage of time that a patient is in an upright position while also exceeding a predetermine amount of acceleration (which can be indicative of the patient walking, running, riding a bicycle or moving up or down stairs). These are just a few examples of how the data (indicative of the at least two dimensions of activity monitored using the active activity sensor) and timing information can be analyzed to quantify a patient's level of activity.

Step 408 can be performed, e.g., by a processor or other type of controller within the implantable device. Additionally, or alternatively, the data and timing information stored at step 406 can be uploaded (e.g., using telemetry) when a patient visits their physician, thereby enabling the physician (or the physician's computer) to analyze the patient's activity, e.g., since the patient's last visit. The data and timing information can provide complex and informative trends about a patient's physical activity, or lack thereof. As explained above, such information may be indicative of how often the patient is active over a period of time, or even how often the patient is lying down, sitting up, walking and/or running. This type of information may be very beneficial to a physician that is monitoring the progression of a disease, such as CHF.

Returning to FIG. 4, at step 410, an alert is triggered in response to a determination that the patient's prolonged activity level drops below a specified level. In some embodiments, the alert is a patient alert. Such an alert could be a vibratory or auditory alert that originates from within an implantable device. Alternatively or additionally, an implantable device may wirelessly transmit an alert to an external device that produces a visual or auditory alert that a patient can see or hear. The alert may inform that patient that he should visit his physician, take medication and/or increase his exercise level. Alternatively or additionally, a physician or other person (e.g., a caregiver, guardian or relative of the patient) is alerted whenever the patient's prolonged activity level drops below a specified level.

In alternative embodiments of the present invention, rather than using the output of a passive activity sensor to trigger use of a multi-dimensional active activity sensor, other low power sensors used on a relatively continuous basis can be used to trigger the use of the relatively high power active activity sensor. More specifically, in accordance with embodiments of the present invention, the low power sensor can be a photo-plethysmography (PPG) sensor or other type of pulse oxymetry sensor that is used to monitor oxygen saturation. Such an embodiment will be described with reference to FIG. 5.

Referring briefly back to FIG. 3, the device 110' is also shown is including on oxygen saturation sensor 322, which, e.g., can be a PPG sensor. Such a PPG sensor generally includes a light source that generates light of two wavelengths (e.g., 660 nm and 940 nm) and a light detector. Exemplary implantable PPG sensors capable of being used to measure oxygen saturation levels are disclosed in U.S. Pat. No. 6,491,639 (Turcott) and U.S. Pat. No. 6,480,733 (Turcott), which are incorporated herein by reference.

Figure 5:
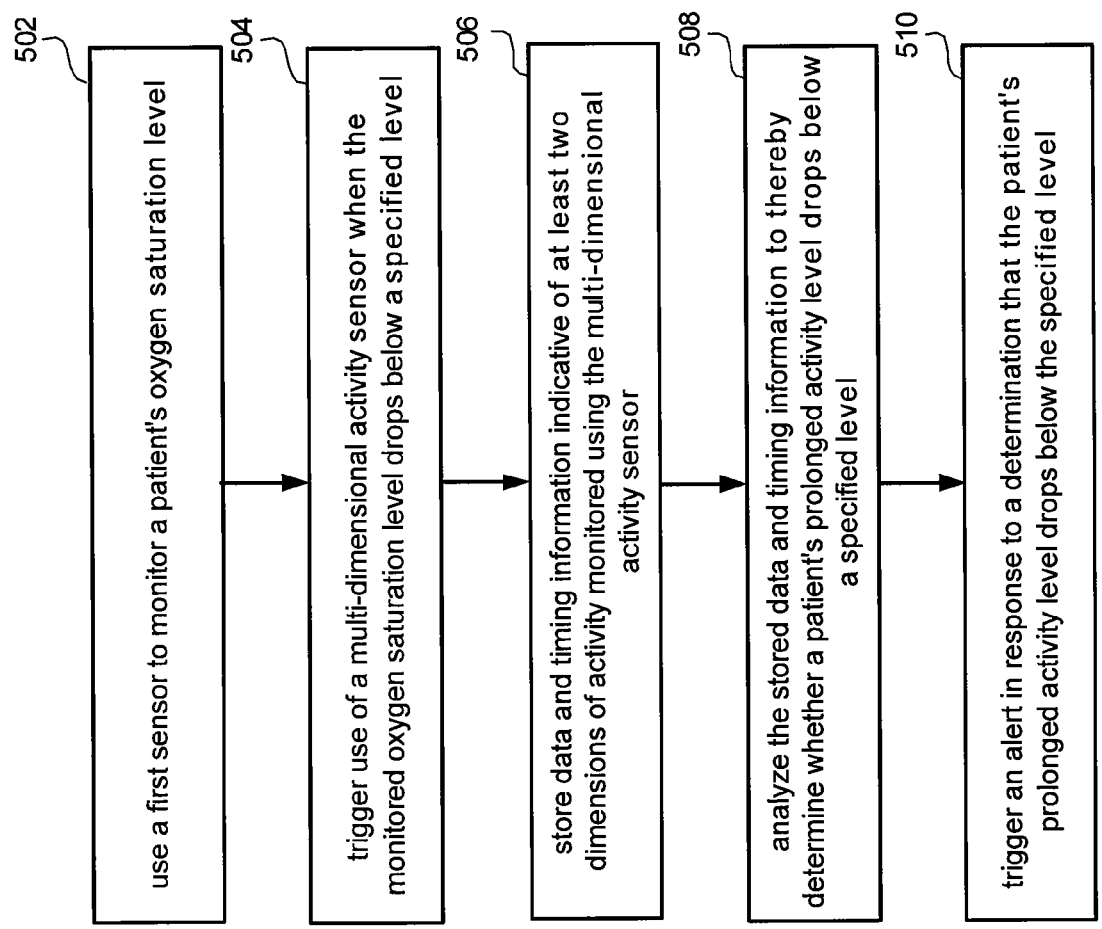

Referring to FIG. 5, at a step 502, a low power sensor is used to monitor a patient's oxygen saturation level. As mentioned above, the low power sensor can be a PPG sensor (e.g., 322) or some other type of oxygen saturation sensor.

At step 504, the use of a relatively high power multi-dimensional activity sensor is triggered when the monitored oxygen saturation level drops below a specified level (e.g., 90%), which may be indicative of hypopnea. In some cases, this periodic drop in oxygen saturation may be the result of the onset of a pulmonary edema. As with step 404, once enabled, the multi-dimensional sensor need only be enabled long enough (e.g., 10 seconds) that the signal(s) produced by the active activity sensor contain enough information to determine the dimensions of patient activity that are of interest. Steps 506-510 are similar to steps 406-410, and thus need not be described in detail. By collecting multi-dimensional activity data whenever a patient's oxygen saturation level drops below a certain level, the progression or regression of CHF (and/or other diseases) can be tracked. More specifically, such information can be used to trigger alerts. Such information can also be used to enhance the administration of therapies and to enable the monitoring of the effectiveness of such therapies.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

The invention claimed is:

1. A method for use with an implantable cardiac stimulation device, the method comprising:
   (a) using a first sensor to monitor a patient's oxygen saturation level, wherein said first sensor requires a first external excitation current to monitor oxygen saturation level; and
   (b) triggering use of a multi-dimensional activity sensor for a pre-defined period of time when the monitored oxygen saturation level drops below a specified level,
   wherein the multi-dimensional activity sensor monitors at least two dimensions of activity that are useful for monitoring disease progression, and
   wherein the multi-dimensional activity sensor requires a second excitation current to produce one or more signal indicative of the at least two dimensions of activity, the second excitation current being greater than the first external excitation current.

2. The method of claim 1, further comprising:
   (c) storing data and timing information indicative of the at least two dimensions of activity monitored using the multi-dimensional activity sensor.

3. The method of claim 2, further comprising:
   (d) analyzing the stored data and timing information to thereby determine whether a patient's activity level for a period of time drops below a specified level.

4. The method of claim 3, further comprising:
   (e) triggering an alert in response to a determination that the patient's activity level for a period of time drops below the specified level.

5. The method of claim 1, wherein the multi-dimensional activity sensor monitors at least two dimensions of activity indicative of two or more of acceleration, direction, posture and tilt.

6. The method of claim 5, wherein in step (b) the period of time, for which use of the multi-dimensional activity sensor is triggered, is approximately only long enough such that the one or more signal produced by the multi-dimensional activity sensor includes enough information to determine the at least two dimensions of activity.

7. The method of claim 1, wherein in step (b) the period of time, for which use of the multi-dimensional activity sensor is triggered, is approximately only long enough such that the one or more signal produced by the multi-dimensional activity sensor includes enough information to determine the at least two dimensions of activity.

8. An implantable cardiac stimulation device, comprising:
   a first sensor that monitors a patient's oxygen saturation level, wherein said first sensor requires a first external excitation current to monitor oxygen saturation level; and
   a multi-dimensional activity sensor that monitors at least two dimensions of activity that are useful for monitoring disease progression,
   wherein the multi-dimensional activity sensor requires a second excitation current to produce one or more signal indicative of the at least two dimensions of activity, the second excitation current being greater than the first external excitation current; and
   wherein temporary use of the multi-dimensional activity sensor for a pre-defined period of time is triggered when the monitored oxygen saturation level drops below a specified level.

9. The device of claim 8, further comprising:
   means for storing data and timing information indicative of the at least two dimensions of activity monitored using the multi-dimensional activity sensor.

10. The device of claim 9, further comprising:
    means for analyzing the stored data and timing information to thereby determine whether a patient's activity level for a period of time drops below a specified level.

11. The device of claim 10, further comprising:
    an alert that is triggered in response to a determination that the patient's activity level for a period of time drops below the specified level.

12. The device of claim 8, wherein the multi-dimensional activity sensor monitors at least two dimensions of activity indicative of two or more of acceleration, direction, posture and tilt.

13. The device of claim 12, wherein the period of time, for which temporary use of the multi-dimensional activity sensor is triggered, is approximately only long enough such that the one or more signal produced by the multi-dimensional activity sensor includes enough information to determine the at least two dimensions of activity.

14. The device of claim 8, wherein the period of time, for which temporary use of the multi-dimensional activity sensor is triggered, is approximately only long enough such that the one or more signal produced by the multi-dimensional activity sensor includes enough information to determine the at least two dimensions of activity.

15. A method for use with an implantable cardiac stimulation device, the method comprising:
   (a) using a first sensor to monitor a patient's oxygen saturation level, wherein said first sensor requires a first external excitation current to monitor oxygen saturation level; and
   (b) in response to the monitored oxygen saturation level dropping below a specified oxygen saturation threshold, triggering use of a multi-dimensional activity sensor for a period of time that is approximately only long enough to obtain a threshold amount of information indicative of a specified at least two dimensions of activity;
   wherein the multi-dimensional activity sensor requires a second excitation current to obtain the information indicative of the specified at least two dimensions of activity, the second excitation current being greater than the first external excitation current.

16. The method of claim 15, further comprising:
   (c) storing the obtained information indicative of the specified at least two dimensions of activity.

17. The method of claim 16, further comprising:
   (d) analyzing the stored information to thereby determine whether a patient's activity level for a period of time drops below a specified level.

18. The method of claim 17, further comprising:
   (e) triggering an alert in response to a determination that the patient's activity level for a period of time drops below the specified level.

19. The method of claim 15, wherein the specified at least two dimensions of activity include two or more of acceleration, direction, posture and tilt.

* * * * *